(12) United States Patent
Kruglick (10) Patent No.: US 9,682,156 B2
(45) Date of Patent: Jun. 20, 2017

(54) PARTICLES WITH RADIATION ACTIVATED ADHESIVE

(75) Inventor: Ezekiel Kruglick, Poway, CA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 1556 days.

(21) Appl. No.: 12/580,940

(22) Filed: Oct. 16, 2009

(65) Prior Publication Data

US 2011/0091389 A1    Apr. 21, 2011

(51) Int. Cl.
| | |
|---|---|
| A61K 49/04 | (2006.01) |
| A61K 41/00 | (2006.01) |
| A61K 49/18 | (2006.01) |
| B22F 1/02 | (2006.01) |
| B82Y 5/00 | (2011.01) |
| B22F 1/00 | (2006.01) |
| B82Y 30/00 | (2011.01) |
| C22C 5/02 | (2006.01) |
| C22C 28/00 | (2006.01) |

(52) U.S. Cl.
CPC ...... *A61K 49/0423* (2013.01); *A61K 41/0052* (2013.01); *A61K 49/1827* (2013.01); *B22F 1/0022* (2013.01); *B22F 1/02* (2013.01); *B82Y 5/00* (2013.01); *B82Y 30/00* (2013.01); *C22C 5/02* (2013.01); *C22C 28/00* (2013.01); *B22F 2202/11* (2013.01); *Y10T 428/12181* (2015.01); *Y10T 428/2991* (2015.01)

(58) Field of Classification Search
None
See application file for complete search history.

(56) References Cited

U.S. PATENT DOCUMENTS

| | | | | |
|---|---|---|---|---|
| 5,098,426 | A * | 3/1992 | Sklar et al. | 606/5 |
| 5,873,811 | A * | 2/1999 | Wang et al. | 600/3 |
| 6,685,730 | B2 * | 2/2004 | West et al. | 607/89 |
| 6,919,067 | B2 * | 7/2005 | Filler et al. | 424/1.29 |
| 6,939,364 | B1 * | 9/2005 | Soltz et al. | 606/214 |
| 7,893,384 | B2 * | 2/2011 | Lin | B23K 26/03 219/121.68 |
| 2002/0103517 | A1 * | 8/2002 | West et al. | 607/88 |
| 2004/0171924 | A1 * | 9/2004 | Mire et al. | 600/407 |
| 2008/0262390 | A1 * | 10/2008 | Bangera | A61B 17/0401 600/587 |
| 2008/0279946 | A1 * | 11/2008 | Hainfeld | A61K 33/24 424/489 |
| 2010/0137241 | A1 * | 6/2010 | Elisseeff | A61L 24/0031 514/54 |

FOREIGN PATENT DOCUMENTS

WO    WO 2008036763 A2 *  3/2008

OTHER PUBLICATIONS

Gobin, A., et al., "Near Infrared Laser—Tissue Welding Using Nanoshells as an Exogenous Absorber", 2005, Lasers in Surgery and Medicine, 37, pp. 123-129.*
Schiffner, D.C., et al., "Daily Electronic Portal Imaging of Implanted Gold Seed Fiducials in Patients Undergoing Radiotherapy After Radical Prostatectomy", 2007, Int. J. Rad. Onc. Biol. Phys., 67, pp. 610-619.*
Hanes, J., et al., "Synthesis and Characterization of Degradable Anhydride-co-imide Terpolymers Containing Trimellitylimido-L-tyrosine: Novel Polymers for Drug Delivery", 1996, Macromolecules, 29, pp. 5279-5287.*
Lim, Y.K. et al., "Microscopic Gold Particle-Based Fiducial Markers for Proton Therapy of Prostate Cancer", Int. J. Radiation Oncology Biol. Phys. Aug. 2009, pp. 1609-1616.*
DeJong et al., "*Particle size-dependent organ distribution of gold nanoparticles after intravenous administration*", Biomaterials, vol. 29, Issue 12, 2008, pp. 1912-1919.
Kitamura et al., "*Registration accuracy and possible migration of internal fiducial gold marker implanted in prostate and liver treated with real-time tumor-tracking radiation therapy (RTRT)*", Radiotherapy and Oncology, vol. 62, 2002, pp. 275-281.
Uhrich et al., "*Synthesis and Characterization of Degradable Poly(anhydride-co-imides)*", Macromolecules, vol. 28, 1995, pp. 2184-2193.

* cited by examiner

Primary Examiner — Michael G Hartley
Assistant Examiner — Lance Rider
(74) *Attorney, Agent, or Firm* — Xinova, LLC (57) ABSTRACT

Techniques are generally described for particles with a surface including an adhesion material. The adhesion material may be selectively activated in response to radiation. The particles may be distributed proximate to a target through a fluid system. Radiation may be emitted toward the target causing the adhesion material to activate. The activated adhesive material on the surface of the particles may adhere to the target providing a fiducial mark or reference point. The fiducial mark may be visible through a medical imaging technique. In some examples, the particles may be nanoparticles. In some examples, the radiation may be infrared radiation.

22 Claims, 8 Drawing Sheets

┌──────────────────────────────┐
│  Providing a plurality of     │── 610
│  particles proximate a target │
└──────────────────────────────┘
              │
              ▼
┌──────────────────────────────┐
│ Emitting radiation toward the │
│ target thereby causing at     │── 620
│ least some of the particles   │
│ to adhere to the target       │
└──────────────────────────────┘
```

PARTICLES WITH RADIATION ACTIVATED ADHESIVE

BACKGROUND

Unless otherwise indicated herein, the materials described in this section are not prior art to the claims in this application and are not admitted to be prior art by inclusion in this section.

Nanoparticles may be used for applying photo-thermal therapy to treat various medical conditions. For instance, gold nanoparticles, in combination with infrared radiation, may be used to apply photothermal therapy to a localized area, such as an organ of a human subject. In particular, gold nanoparticles may be distributed through a subject's body. Infrared radiation may then be projected on the subject's body at the localized area. Gold nanoparticles exposed to the radiation convert the radiation to heat, providing thermal therapy to the localized area of the subject.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings.

In the drawings.

DETAILED DESCRIPTION

The following detailed description, reference is made to the accompanying drawings, which form a part hereof. In the drawings, similar symbols typically identify similar components, unless context dictates otherwise. The illustrative examples described in the detailed description, drawings, and claims are not meant to be limiting. Other examples may be utilized, and other changes may be made, without departing from the spirit or scope of the subject matter presented herein. It will be readily understood that the aspects of the present disclosure, as generally described herein, and illustrated in the Figures, may be arranged, substituted, combined, separated, and designed in a wide variety of different configurations, all of which are implicitly contemplated herein.

This disclosure is drawn, inter alia, to methods, systems, devices, and/or apparatus generally related to particles comprising a radiation activated adhesive on a surface thereof.

Some example devices and methods may utilize techniques described herein to adhere at least a portion of a plurality of particles to a target. In some examples, a plurality of particles may be distributed through a fluid system proximate to a target. A radiation source may be configured to emit radiation on the particles proximate the target to activate the adhesive on the surface of the particles. Once the adhesive on the surface of the particles has been activated, at least some of the particles may adhere to the target. The plurality of particles may be configured to be visible through medical imaging using any of a variety of techniques. In some examples, the particles are nanoparticles. In some examples, the target may be in a live subject. For instance, the target may be a lumen, such as sidewalls of a blood vessel, in and/or on an organ, a tissue, a tumor, or the like within a body of the live subject. In some examples, the adhered particles may be visible under a medical imaging technique. In many examples, the particles may be provided to the live subject intravenously and distributed to the target through blood circulation.

Figure 1:
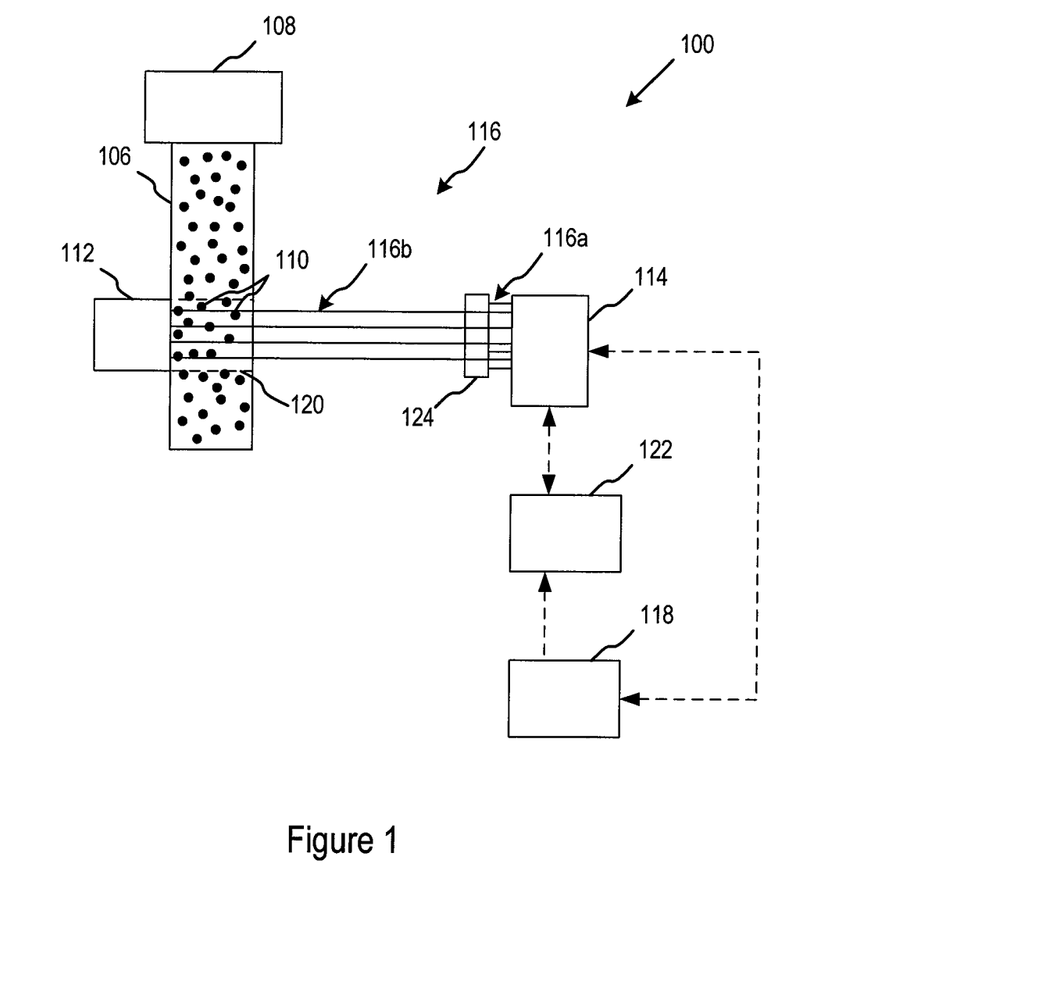
FIG. 1 is a schematic illustration of a system adapted to mark a target.

FIG. 1 is a schematic illustration of a system 100 adapted to mark a target in accordance with at least some examples of the present disclosure. The example system 100 may include a particle source 108, a plurality of particles 110, a target 112, and a radiation source, such as a radiation illuminator 114. Although not illustrated in FIG. 1, the target 112 may be located in a subject, such as a human body or other live subject. In some examples, the target 112 may be a lumen in and/or on a tissue, an organ, a tumor, and/or some other body structure in the live subject.

The particles 110, which include adhesion material, may be distributed proximate to the target 112. In some examples, the particles may be distributed proximate to the target via a fluid system 106. The fluid system 106 may comprise a liquid or a gas. The radiation illuminator 114 may be adapted to selectively and/or contiguously emit radiation 116 toward the target 112. The radiation illuminator 114 may be configured to emit any type of radiation, such as infrared, radio waves, visible light, ultraviolet light, ultrasound, etc. The radiation illuminator 114 emits radiation on a region 120. The adhesion material in at least some of the particles 110 in the region 120 that are proximate to the target are activated in response to the radiation emitted from the radiation illuminator 114. Once the adhesive material is activated, at least some of the particles 110 that are proximate to the target 112 may adhere to the target 112.

The example system may further include a filter 124 configured to block some of the radiation 116 being emitted from the radiation illuminator 114. In particular, the radiation illuminator 114 may be configured to emit two kinds of radiation, such as near-infrared and visible radiation. The filter 124 may be configured to block the visible radiation 116a, but allow the near-infrared radiation 116b through the filter 124.

The particles 110 that are adhered to the target may be used as a fiducial mark. Various medical imaging techniques, which will be further discussed below, may be used to evaluate and/or track any changes associated with the target. For example, the fiducial mark may be an initial reference point that identifies a specific location and/or orientation associated with the target 112, such as might be used as a baseline for evaluating a medical condition. Further medical images may be taken at a later time, or under some other condition such as when a patient undergoes a physical stress or trauma. The medical images can be compared to identify changes in the position and/or orientation associated with the target based on the fiducial mark changing from the reference point to another point.

A processor 118 may be coupled to the radiation illuminator 114. The processor 118 may be configured to cause the radiation illuminator 114 to selectively emit radiation 166 toward the target 112. The amount of radiation emitted from the radiation illuminator 114 may vary and the time duration of emitting the radiation 116 may vary. In one example, the processor 118 may be configured to control the amount of energy and/or the duration that the radiation 116 is emitted from the radiation illuminator 114. For instance, in some examples, the time duration may be contiguous at a particular radiation level or pulsed over an elapsed time. The width of the pulse may be constant, varying, or a combination thereof. The processor 118 may be further configured to control the total radiation exposure time limit and/or energy level.

A movement sensor 122 may be coupled to the radiation illuminator 114 and/or the processor 118. The movement sensor 122 may be configured to detect movement in the target 112. As will be explained in more detail below, the radiation illuminator 114 may emit radiation 116 when the target 112 is still and stop emitting radiation when the target 112 moves. For instance, the movement sensor 122 may be configured to detect movement in the target 112 and transmits a movement signal to the processor 118. Responsive to the movement signal, the processor may transmit a signal to the radiation illuminator 114 that causes the radiation illuminator 114 to stop emitting radiation. Alternatively, the movement sensor 122 may be an imaging device, such as a camera or magnetic resonance imaging (MRI) configured to detect motion in the target.

In some examples, the particles 110 may be any particle having dimensions that are less than about 1 centimeter. For instance, in some examples, the particles are nanoparticles, microparticles, miliparticles or any combination thereof. The particles 110 may be at least partially coated in a radiation activated adhesive material. That is, the adhesive material may remain inactive until it is exposed to the radiation 116. The radiation 116 may activate the adhesive material directly, indirectly or a combination thereof. In the case of directly activating the adhesive material, the radiation directly interacts with the adhesive material to activate the adhesive properties. In some examples, the adhesive material may be directly activated by thermal energy that is sourced from the radiation. Alternatively, in the case of indirectly activating the adhesive material, the radiation 116 may thermally activate the adhesive by heating the particle 110 or nanoparticles, which in turn causes the adhesive properties of the adhesive material to be activated. In this example, the adhesive may remain inactive on the nanoparticles until it is thermally activated. In some examples, the radiation 116 may also activate a thermally activated adhesive material by heating both the nanoparticle and the adhesive material.

The particle may be fabricated to form the adhesive material as a byproduct of the fabrication process of the particle itself. Alternatively, one or more layers of the adhesive material may be applied to an outer surface of the particle 110 after the particle is manufactured. In some examples, the adhesive is a bio-compatible material and/or a polymer material, such as poly-anhydrides-co-imides or other polymer materials.

Figure 2:
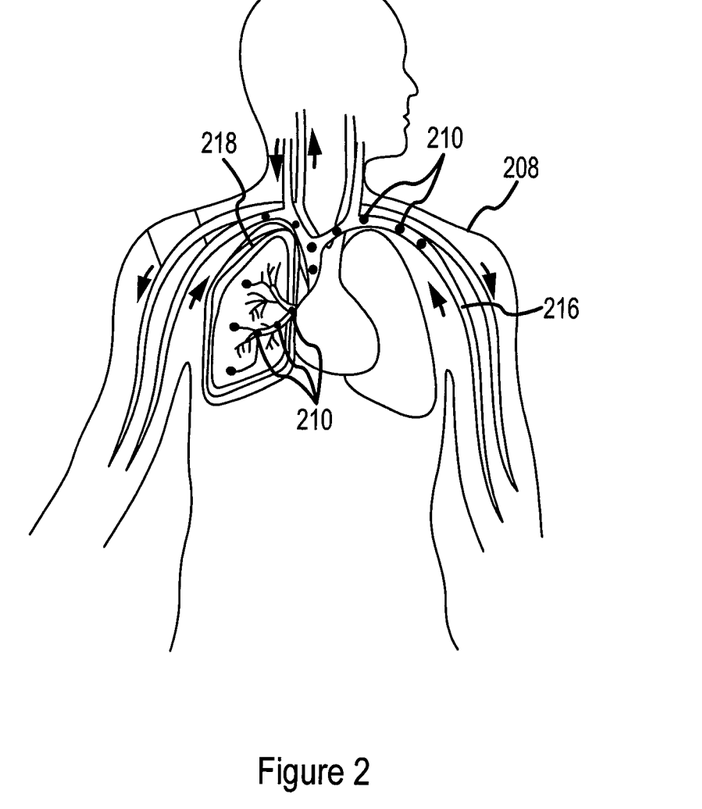
FIG. 2 is a schematic illustration of nanoparticles circulating in the bloodstream of a human subject.

FIG. 2 is a schematic illustration of particles, such as nanoparticles 210, circulating in the bloodstream 216 of a human subject 208 in accordance with at least some examples of the present disclosure. The nanoparticles 210 may be provided to the bloodstream 216 of the human subject 208 intravenously. The bloodstream 216 may circulate the nanoparticles 210 through the body of the subject 208 such that the nanoparticles 210 enter various body structures, such as cells, tissues, organs, glands, tumors, or the like. Example body structures may include blood, liver, spleen, kidney, testis, thymus, heart, lung, brain, etc. The radiation illuminator 114 of FIG. 1 may be configured to project infrared radiation 116 through the skin of the live subject 208 to an intended target. For instance, if the intended target is sidewalls of a blood vessel in and/or on a lung 218 of a subject 208, the radiation illuminator 114 may be arranged to emit infrared radiation through the skin of the subject 208 to the lung 218. As discussed above, the infrared radiation 116 from the radiation illuminator 114 will activate the adhesive material for those nanoparticles 210 that are within range of the infrared radiation 116. Therefore, at least some portion of those nanoparticles 210 having the activated adhesive material that are proximate to the lung may adhere to sidewalls of a blood vessels in and/or on the lung 218. The adhesive bond may be a chemical bond, a mechanical bond, or a hydrogen bond.

The nanoparticles 210 that adhere to the lumen or sidewalls of a blood vessel in and/or on the organ to form a fiducial mark that may act as a body reference point and may provide orientation and location to a medical professional. For example, a fiducial mark on the liver may be used to guide a beam during non-invasive treatments or surgery. The fiducial mark may be used as a mark for receiving the beam. Alternatively, the mark may be a reference point to orient and guide the medical professional within the body. The nanoparticles 210 that adhere to the lumens in and/or on the organ and form the fiducial mark may be visible under imaging systems such as X-ray, magnetic resonance imaging (MRI), or other methods. Once the fiducial mark has been formed (i.e., by activation of the adhesion material), the remaining nanoparticles 210 in the bloodstream 216 may be removed from the bloodstream 216.

Various body structures, such as the liver or the lung, may receive higher concentrations of nanoparticles 210 as nanoparticles are distributed through the bloodstream through blood circulation. Therefore, the amount of nanoparticles 210 distributed to the bloodstream 216 may be varied depending on the target. For instance, the liver is well known to absorb higher concentration levels of nanoparticles 210 than the brain. Therefore, if the liver is the determined target, lower levels of concentration of nanoparticles 210 may be distributed to the bloodstream 216 than if the brain was the target. Concentration levels may range from an order of thousands of nanoparticles per cubic centimeter to 1 nanoparticle per cubic centimeter or less.

The duration at which the nanoparticles 210 are distributed to the target may also depend on which body structure is the target. In general, the nanoparticles 210 may be distributed to the target in manner to prevent the formation of plaque build up or blockages. Therefore, the number of nanoparticles 210 being distributed and the rate at which the nanoparticles 210 are distributed to the target may be sufficiently low to prevent such blockages in the bloodstream. For instance, in some examples, the nanoparticles 210 may be circulated in or distributed to the bloodstream 216 over a period of hours. In some instance, such as when the target is a lung and is, therefore, a moving target, the nanoparticles may be distributed through the bloodstream for up to 8 hours and in some instance for more than 8 hours.

In other examples, the particles may be distributed to the bloodstream for a matter of minutes. The rate at which particles are distributed in the bloodstream may vary depending on the particle size, the target, the injection method of providing the particles into the bloodstream, or any combination thereof.

When used in a live subject, the nanoparticles 210 and the thermally activated adhesive may be made from biocompatible materials. For instance, in many examples, the thermally activated adhesive may be a biocompatible adhesive, such as poly(anhydride-co-imides). Examples of biocompatible adhesives are well known in the art and are further described in Uhrich et al, *Synthesis and Characterization of Degradable Poly(anhydride-co-imides*, Macromolecules 28: 2184-93 (1995), hereby incorporated by reference herein in its entirety for any purpose. The nanoparticle may be formed from a material such that once it adheres to the target to form the fiducial mark, the fiducial mark may be visible under imaging systems such as X-ray, magnetic resonance imaging (MRI), or other methods. Furthermore, the nanoparticles 210 may be a material that does not interfere with some medical imaging techniques such as X-rays, MRIs, gamma knife, and other medical methods. In some examples, the nanoparticles 210 may be gold, gadolinium, or a combination thereof. In other examples, the nanoparticles 210 may be other gold or gadolinium alloys. In yet other examples, the nanoparticles 210 may be other metals, glass, plastic, or a particle of some other type of material. In other examples, the nanoparticle is the adhesive material itself.

The size of the nanoparticles 210 may vary depending on the target. For instance, nanoparticles having a maximum dimension of approximately 10 nm or less may easily enter body structures associated with blood, liver, spleen, kidney, testis, thymus, heart, lung, and/or brain. Suitable nanoparticles sizes in relation to bodily distribution has been studied and examples may be found in De Jong et al, *Particle Size-dependent Organ Distribution of Gold Nanoparticles After Intravenous Administration*, Biomaterials Volume 29, Issue 12, April 2008, pages 1912-1919, hereby incorporated by reference in its entirety for any purpose. The nanoparticle may have a maximum dimension larger than approximately $10^{-9}$ meters. In some instance, the nanoparticles may have a maximum dimension between 1 nm and 100 nm. In some examples, the maximum dimension may be a length for a rod shaped nanoparticle or a diameter for a sphere shaped particle.

As indicated above with reference to FIG. 1, a filter that prevents transmission of radiation other than an intended radiation, such as infrared radiation, may be used. For instance, a filter may be used to prevent visible light from being emitting. This may assist in preventing heat from being applied to the surface of the subject's skin, causing discomfort to a live subject. Other types of radiation may also be filtered as may be desired in a particular example implementation. For instance, x-rays or radio wave radiation may be filtered out in some example systems.

In some examples, the infrared radiation may compensate for biological activity of the live subject. For instance, the infrared radiation may be projected in a manner that coincides with the movement of a biological target, such as the movement of an organ. In some examples, the infrared radiation may be provided intermittently to accommodate biological movement of the target via a processor (such as that described in FIG. 1) that is adapted in accordance with various methods or processes that turn on and off the radiation illuminator or other radiation energy source. For instance, assuming the target is a human lung, as the subject breathes, the precise location of the target may vary. A movement sensor, such as the movement sensor 122 in FIG. 1, may be adapted to detect when the lung is expanded. Therefore, the system may adaptively control the infrared illuminator such that infrared radiation is emitted towards the lung (the target) while the lung is expanded and infrared radiation is not emitted towards the lung when the lung is contracted.

The infrared radiation may be projected at low levels over an extended period of time sufficient to prevent the formation of plaque or blockages. For instance, a small number of nanoparticles may be selectively activated at a particular time so that the total number of nanoparticles activated at that particular time does not result in the formation of a hazardous blockage. In some examples, the infrared radiation may be near-infrared radiation. Once the target site has been sufficiently marked, the remaining nanoparticles may be flushed out of the body. In some examples, the fiducial mark may remain on the target for extended time periods, thus facilitating long-term diagnostic observations and comparisons. That is, the fiducial mark may be used to track morphological changes in the live subject that may occur overtime or when subject to a physical stress or other condition. For example, the fiducial mark may be used to track enlargement or shrinkage of an organ or a tumor over time. This may be used to facilitate calculating a rate at which a tumor, organ, or other internal features grow or shrink.

Figure 3:
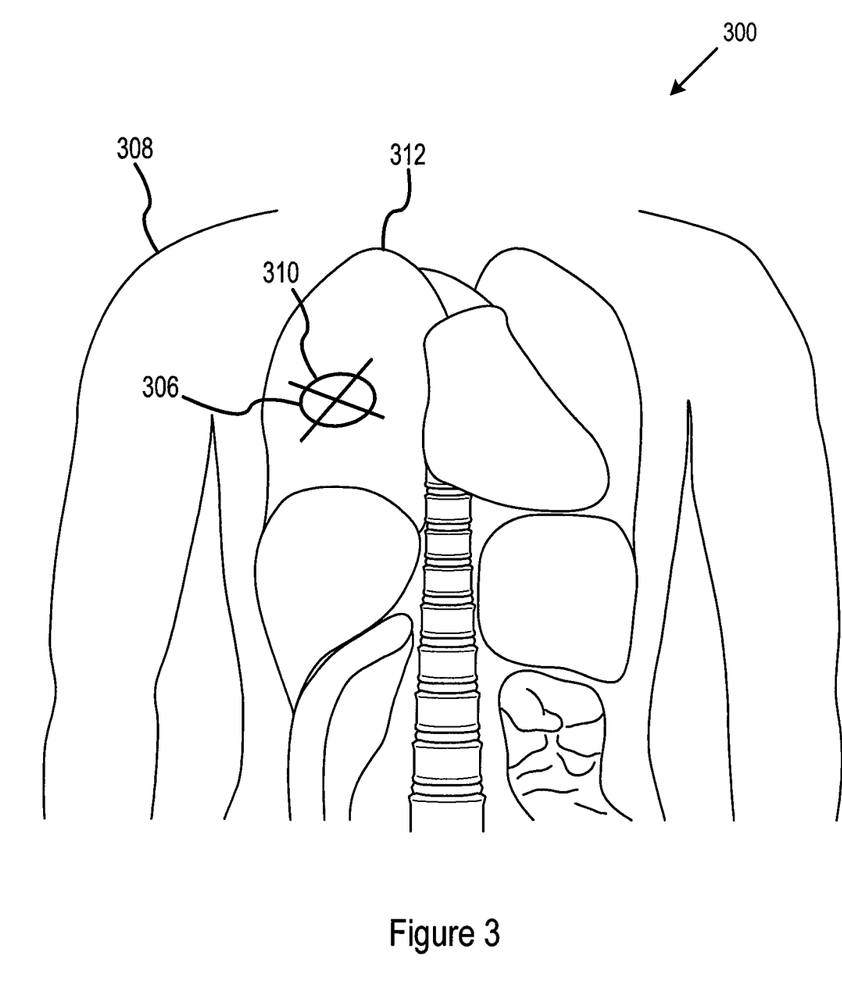
FIG. 3 is a schematic illustration of nanoparticles secured to a target in a human subject.

FIG. 3 is a schematic illustration 300 of nanoparticles 310 adhering to a target in a human subject 308 in accordance with at least some examples of the present disclosure. The schematic illustration 300 may be representative of an MRI image. The target in this example is a lung 312. As is illustrated in FIG. 3, the nanoparticles 310 may adhere to the lung 312 to form a fiducial mark 306. The fiducial mark 306 in this example is a circle with an X-shaped mark formed therein (although any other appropriate/desired shape can be utilized). The fiducial mark 306 may move with the lung 312 as the lung 312 expands and contracts. The fiducial mark 306 may be used to track morphological changes in the lung 312 over long periods of time. For instance, the fiducial mark 306 may be used to track the size of the lung 312 over time to detect growth, shrinkage, or some other phenomena that may cause movement of the position and/or alignment of the fiducial mark 306.

The fiducial mark 306 may be used as a guide or reference point during non-invasive treatment. In some examples, the fiducial mark 306 may be visible under imaging techniques such as X-ray, MRI, or the like. Furthermore, in many examples, the fiducial mark may not be disruptive during such imaging. In one example, the fiducial mark 306 may first be characterized with a detailed imaging system such as MRI. Then the fiducial mark 306 may be used to guide beams, such as particle beams, or other therapy using an X-ray image. The fiducial mark 306 may provide an internal reference point that may orient a medical practitioner. In some examples, characterizing the fiducial mark 306 may further include generating a 3D model of internal portions of the human body including the fiducial mark 306. The various methods and/or processes for assisting the medical practitioner using the fiducial mark 306 may be either manual or automated. For automated methods and/or processes, a computing device or other similar processor based systems may be arranged to monitor/key off of the fiducial mark 306.

Figure 4:
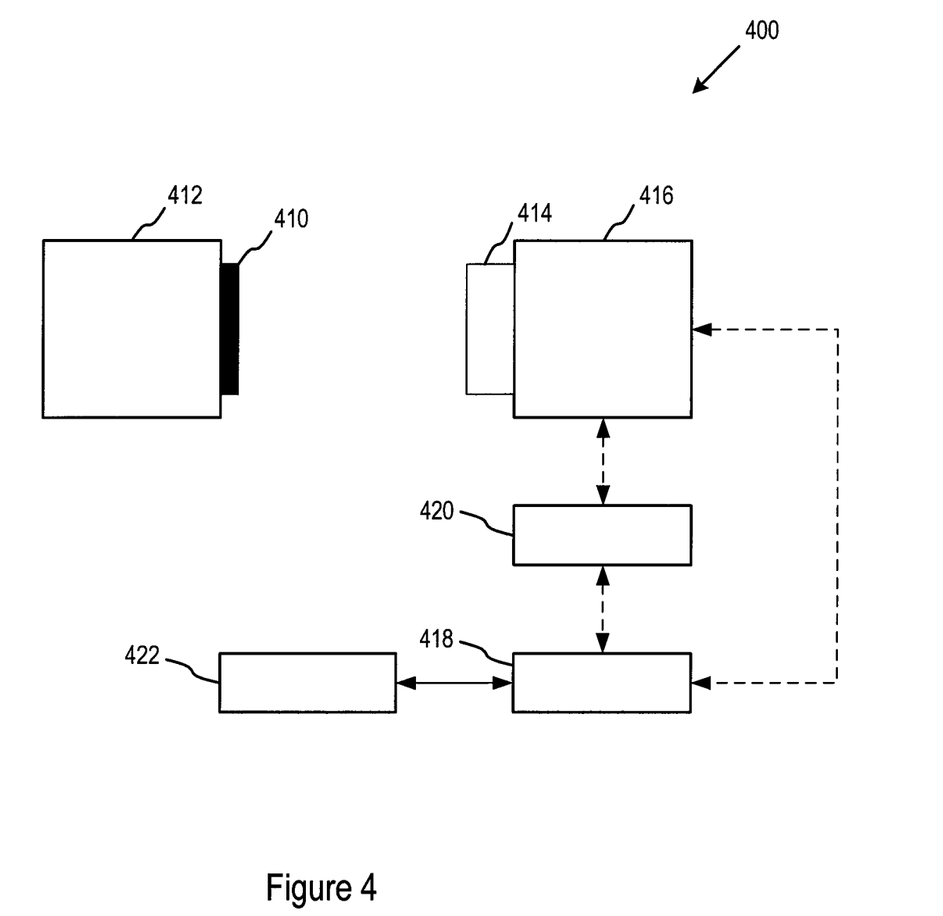
FIG. 4 is a block diagram of a system for imaging a fiducial mark on a target.

FIG. 4 is a schematic illustration of a system 400 for imaging a fiducial mark 410 on a target 412 in accordance with at least some examples of the present disclosure. The example system 400 may include an imaging source 416 adapted to provide an image of at least a portion of the target 412 and the fiducial mark 410. In particular, the image source 416 may include an effective area 414 that may be aligned with at least a portion of the fiducial mark 410 on the target 112. The imaging source 416 may be any medical imaging device being used now or in the future that is adapted to provide an image of the fiducial mark and target, such as an MRI or X-ray device. The example system 400 may include a processor 418, a movement sensor 420, and/or a memory 422. The processor 418 may be coupled to the imaging source 416 and may be configured to control the amount of energy emitted from the imaging source 416. The movement sensor 420 may be coupled to the processor 418 and/or the imaging source 416. The movement sensor 420 may be adapted to sense movement of the fiducial mark 410 on the target 412. The processor 418 may be adapted to adjust the amount of energy emitted from the imaging source in response to movement sensed by the movement sensor 420. A memory 422 may be coupled to the processor 418 and configured to store the data image. The memory 422 may be further configured to store a reference image of the target 412 itself or the target 412 and fiducial mark 410 taken previously. The memory 422 may be further configured to store settings for imaging the fiducial mark 410, such as power level of the imaging source, duration of exposure, total amount of energy transmitted, etc.

Figure 5:
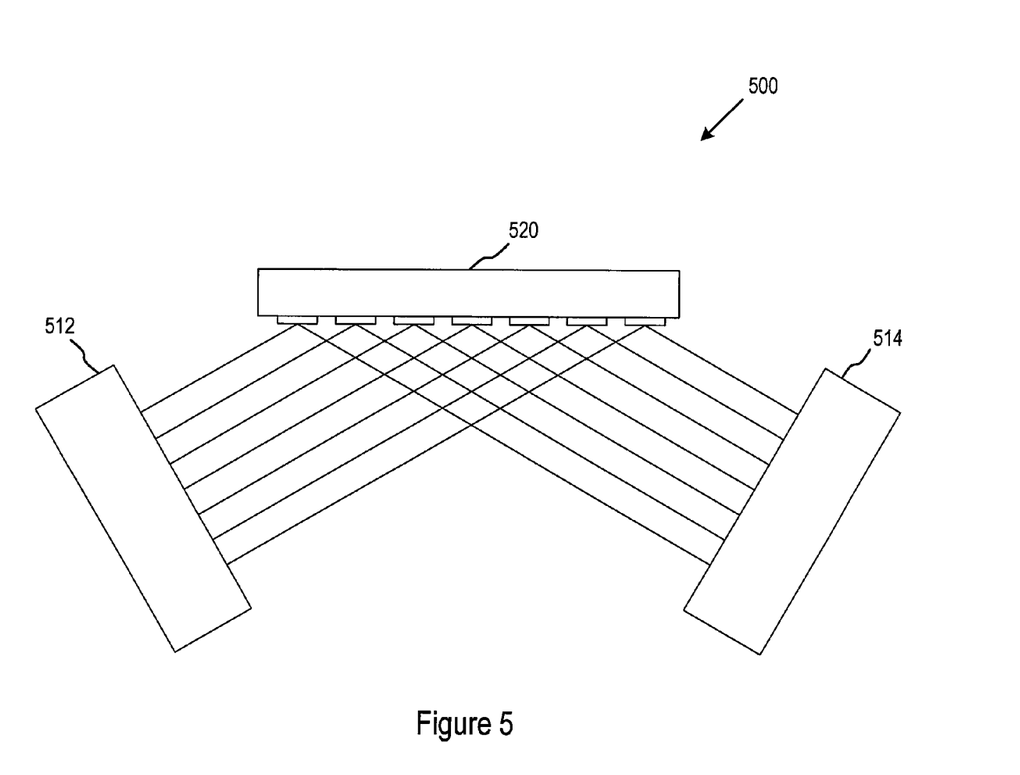
FIG. 5 is a schematic illustration of a system adapted to mark a target.

FIG. 5 is a schematic illustration of a system 500 adapted to mark a target 512 in accordance with at least some examples of the present disclosure. At least some of the components in the system 500 may be used in the system 100 from FIG. 1. For instance, the example system 500 may include a particle source 108, particles 110, a filter 124, etc. as is illustrated in FIG. 1. The example system 500 may include a target 512, a reflective device 520, and a radiation illuminator 514. The reflective device 520 may be arranged to reflect the radiation emitted from the radiation illuminator 514 onto the target 512. The reflective device 520 may comprise reflective components arranged in an intended pattern. The reflective device 520 may be arranged to receive the radiation from the radiation illuminator 514 and reflect the radiation in the form of the pattern onto the intended target 512. Thus, the fiducial mark may take the form of the pattern on the reflective device 520. The reflective device 520 in the example system 500 may be a micro-mirror array. However, other reflective devices 500 may be used, such as, for example, a transmissive LCD imager. The intended pattern may take any form or shape. In some examples, the intended pattern is an X-shaped mark, a plus-shaped mark (e.g., +), a cross-hairs-shaped mark (e.g., ✦), a square-shaped mark (e.g., ☐), a circular or oval-shaped mark, any other shaped mark, or combination thereof. In these examples, the fiducial mark may take the shape of the emitted pattern. The fiducial mark may provide not only position but also orientation (e.g., rotational orientation, possibly an orientation in multiple dimensions). In other examples, the reflective device 520 may be a dynamic reflective device, such as a digital mirror device. In this example, a sensor, such as a movement sensor, detects movement in the target, the pattern of the fiducial mark may change shape, such as from an X fiducial mark to a square fiducial mark. Thus, the fiducial mark may be dynamic and thus modified in response to movement of the target.

Figure 6:
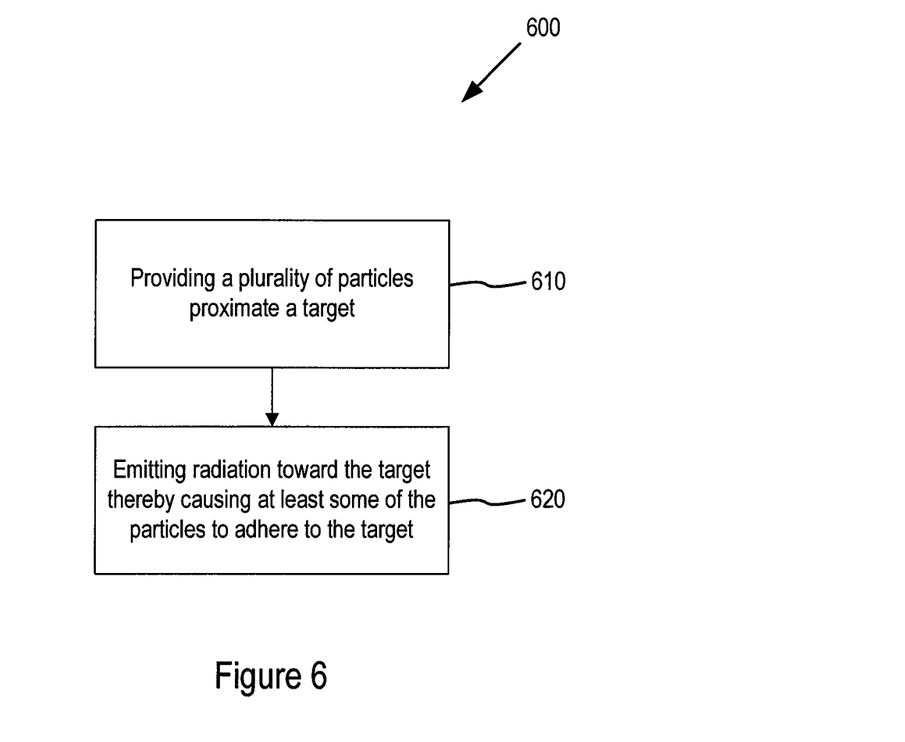
FIG. 6 is a flow chart illustrating a method of securing nanoparticles to a target.

FIG. 6 is a flow chart illustrating an example method 600 of adhering nanoparticles to a target in accordance with at least some examples of the present disclosure. The method 600 may include one or more functions, operations, or actions as illustrated by blocks 610 and/or 620. The example method may begin at block 610. In block 610, a plurality of particles may be provided proximate to a target. Block 610 may be followed by block 620. In block 620, radiation may be emitted toward the target (e.g., by a radiation source) to thermally activate adhesive material on the surface of the plurality of particles that are proximate to the target thereby causing at least some of the particles to adhere to the target. The method 600 may be performed in an order or combination other than is illustrated and may include steps not shown. For instance, radiation may be emitted toward the target before, after, or while the plurality of particles are being provided proximate a target.

As generally described above (see discussion of FIGS. 1 and 2), the nanoparticles may be distributed sufficiently proximate the target to adhere to the target once the adhesive is thermally activated. In some examples, the target is within a body of a live subject. In these examples, the infrared radiation (or some other variety of radiation) may be emitted through the skin of the live subject to the target site. The amount of infrared radiation may be controlled (e.g., via a computing device) to prevent the formation of plaque and blockages. In some examples, a low level of infrared radiation is used over a long period of time.

Figure 7:
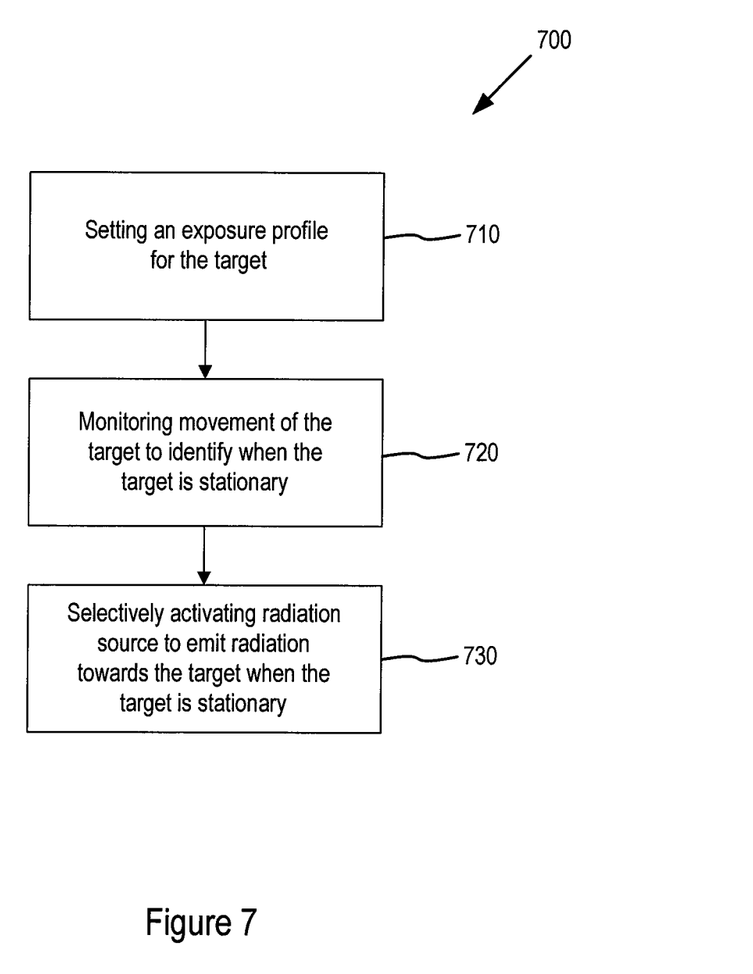
FIG. 7 is a flow chart illustrating an example method of emitting radiation toward a moving target.

FIG. 7 is a flow chart illustrating an example method of emitting radiation toward a moving target in accordance with at least some examples of the present disclosure. The method 700 may include one or more functions, operations, or actions as illustrated by blocks 710, 720, and/or 730. The example method may begin at block 710. In block 710, an exposure profile may be set for the target. The exposure profile may include a variety of parameters, such as an energy level associated with a radiation source, a time or duration for exposure at a particular energy level, a period or pulse width for exposing at a particular energy level, a total radiation exposure time, a total energy exposure level, or the like, or any combination thereof. Block 710 may be followed by block 720. In block 720, movement of the target may be monitored. Block 720 may be followed by block 730. In block 730, the radiation source may be selectively activated when the target is not moving. For instance, the radiation source may activate at set levels and times when the patient is not moving. Once one or more parameters in the exposure profile are met, the process may be terminated. For instance, in one example method, the process is terminated when the radiation energy limit is reached or when the total exposure time has expired. The method 700 may be performed in an order or combination other than is illustrated and may include additional blocks not shown.

Figure 8:
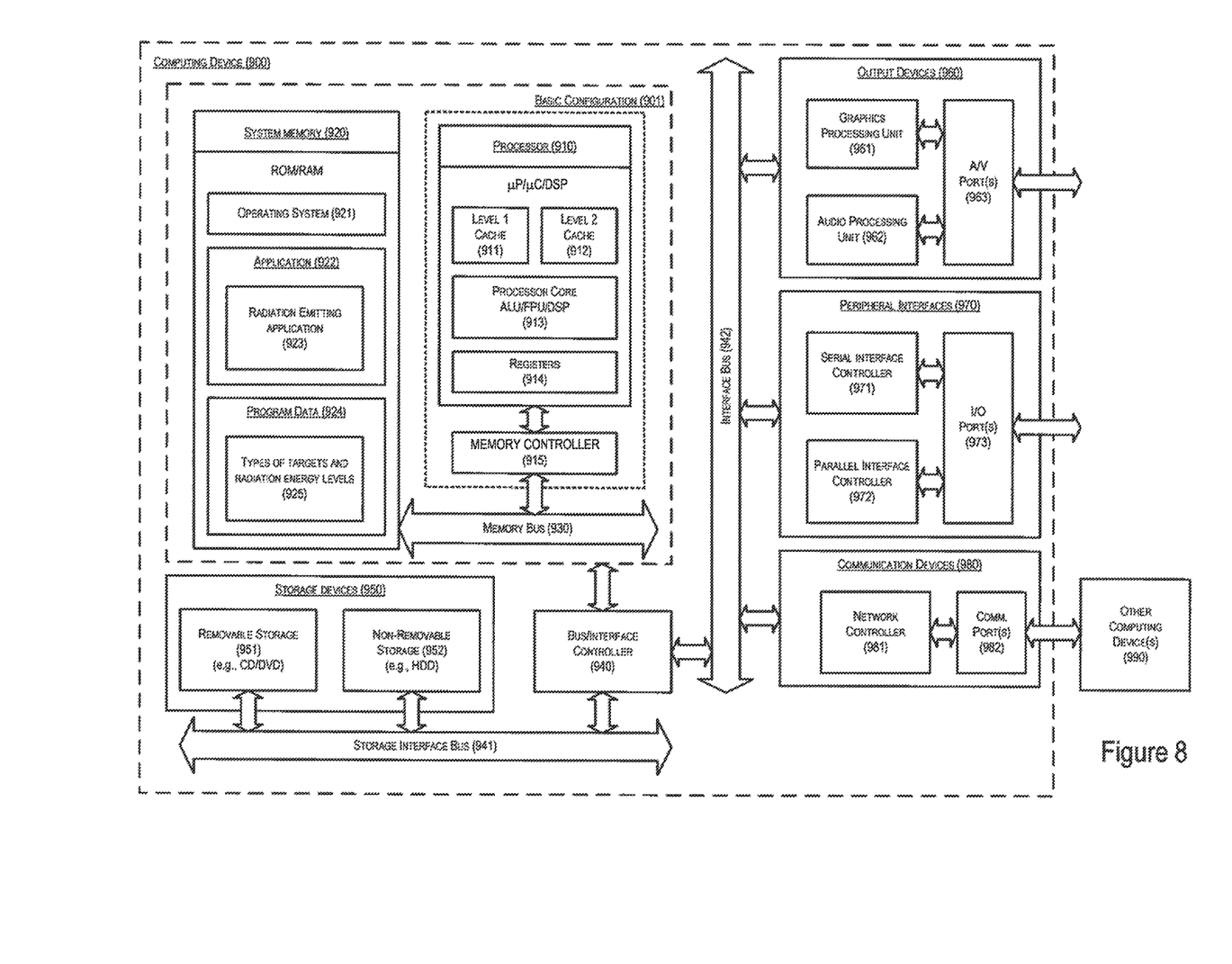
FIG. 8 is a block diagram illustrating an example computing device 900 that may be arranged for adapting to mark a target and/or imaging a target; all arranged in accordance with at least some examples of the present disclosure.

FIG. 8 is a block diagram illustrating an example computing device 900 that may be arranged for adapting to mark a target and/or imaging a target in accordance with at least some examples of the present disclosure. In a very basic configuration 901, computing device 900 typically may include one or more processors 910 and system memory 920. A memory bus 930 may be used for communicating between the processor 910 and the system memory 920.

Depending on the desired configuration, processor 910 may be of any type including but not limited to a microprocessor (μP), a microcontroller (μC), a digital signal processor (DSP), or any combination thereof. Processor 910 may include one or more levels of caching, such as a level one cache 911 and a level two cache 912, a processor core 913, and registers 914. An example processor core 913 may include an arithmetic logic unit (ALU), a floating point unit (FPU), a digital signal processing core (DSP Core), or any combination thereof. An example memory controller 915 may also be used with the processor 910, or in some implementations, the memory controller 915 may be an internal part of the processor 910.

Depending on the desired configuration, the system memory 920 may be of any type including but not limited to volatile memory (such as RAM), non-volatile memory (such as ROM, flash memory, etc.) or any combination thereof. System memory 920 may include an operating system 921, one or more applications 922, and program data 924. Application 922 may include a radiation emitting application 923 that may be arranged to generate an exposure profile for an intended subject and monitor movement and exposure to the subject. The application may be configured to receive signals indicative of movement of the intended target, signals indicative of when a radiation source has reached a particular energy level, signals relating to the time and/or duration of radiation emitted. The application may be further configured to generate signals to cause the radiation source to pulse or set exposure times. Program Data 924 may include types of targets and radiation energy levels associated with particular targets 925 that is useful for determining the appropriate energy level for an intended target, as will be further described below. In some embodiments, application 922 may be arranged to operate with program data 924 on an operating system 921 in accordance with one or more of the techniques, methods, and/or processes described herein. This described basic configuration is illustrated in FIG. 9 by those components within dashed line 901.

Computing device 900 may have additional features or functionality, and additional interfaces to facilitate communications between the basic configuration 901 and any required devices and interfaces. For example, a bus/interface controller 940 may be used to facilitate communications between the basic configuration 901 and one or more data storage devices 950 via a storage interface bus 941. The data storage devices 950 may be removable storage devices 951, non-removable storage devices 952, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 920, removable storage 951 and non-removable storage 952 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 900. Any such computer storage media may be part of computing device 900.

Computing device 900 may also include an interface bus 942 for facilitating communication from various interface devices (e.g., output interfaces, peripheral interfaces, and communication interfaces) to the basic configuration 901 via the bus/interface controller 940. Example output devices 960 include a graphics processing unit 961 and an audio processing unit 962, which may be configured to communicate to various external devices such as a display or speakers via one or more A/V ports 963. Example peripheral interfaces 970 include a serial interface controller 971 or a parallel interface controller 972, which may be configured to communicate with external devices such as input devices (e.g., keyboard, mouse, pen, voice input device, touch input device, etc.) or other peripheral devices (e.g., printer, scanner, etc.) via one or more I/O ports 973. An example communication device 980 includes a network controller 981, which may be arranged to facilitate communications with one or more other computing devices 990 over a network communication link via one or more communication ports 982.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 900 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 900 may also be implemented as a personal computer including both laptop computer and non-laptop computer configurations.

The present disclosure is not to be limited in terms of the particular examples described in this application, which are intended as illustrations of various aspects. Many modifications and examples may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and examples are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which may, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range may be easily recognized as sufficiently describing and enabling the same range being broken down into at least equal halves, thirds, quarters, fifths, tenths, etc. As a non-limiting example, each range discussed herein may be readily broken down into a lower third, middle third and upper third, etc. As will also be understood by one skilled in the art all language such as "up to," "at least," "greater than," "less than," and the like include the number recited and refer to ranges which may be subsequently broken down into subranges as discussed above. Finally, as will be understood by one skilled in the art, a range includes each individual member. Thus, for example, a group having 1-3 items refers to groups having 1, 2, or 3 items. Similarly, a group having 1-5 items refers to groups having 1, 2, 3, 4, or 5 items, and so forth.

While the foregoing detailed description has set forth various examples of the devices and/or processes via the use of block diagrams, flowcharts, and/or examples, such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. For example, if a user determines that speed and accuracy are paramount, the user may opt for mainly hardware and/or firmware vehicle; if flexibility is paramount, the user may opt for mainly software implementation; or, yet again alternatively, the user may opt for some combination of hardware, software, and/or firmware.

In addition, those skilled in the art will appreciate that the mechanisms of the subject matter described herein are capable of being distributed as a program product in a variety of forms, and that an illustrative example of the subject matter described herein applies regardless of the particular type of signal bearing medium used to actually carry out the distribution. Examples of a signal bearing medium include, but are not limited to, the following: a recordable type medium such as a floppy disk, a hard disk drive (HDD), a Compact Disc (CD), a Digital Video Disk (DVD), a digital tape, a computer memory, etc.; and a transmission type medium such as a digital and/or an analog communication medium (e.g., a fiber optic cable, a waveguide, a wired communication link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While various aspects and examples have been disclosed herein, other aspects and examples will be apparent to those skilled in the art. The various aspects and examples disclosed herein are for purposes of illustration and are not intended to be limiting, with the true scope and spirit being indicated by the following claims.

What is claimed is:

1. A method of forming a visual fiducial mark on a target, the method comprising:
   intravenously providing a plurality of particles, wherein a surface of each of the plurality of particles is at least partially coated with a coating consisting of an adhesive that is selectively activated in response to radiation;
   patterning radiation from a radiation source into a predetermined pattern of radiation indicative of the visual fiducial mark; and
   circulating the plurality of particles until at least some of the plurality of particles are selectively adhered to the target b emitting the radiation toward the target in the predetermined pattern of radiation to activate adhesive on respective surfaces of the at least some of the plurality of particles proximate to the target thereby causing the at least some of the plurality of particles proximate to the target to adhere to the target as the visual fiducial mark having the predetermined pattern.

2. The method of claim 1, wherein the plurality of particles comprise a plurality of nanoparticles.

3. The method of claim 1, wherein emitting the radiation toward the target comprises emitting an infrared radiation toward the target.

4. The method of claim 3, wherein emitting the infrared radiation toward the target comprises selectively emitting the infrared radiation toward the target.

5. The method of claim 1, wherein the target comprises a sidewall of a blood vessel in and/or on one or more of an organ, a tissue, and/or a tumor, and wherein providing the plurality of particles proximate to the target comprises distributing the plurality of particles through a portion of a body of a subject in a region of the body proximate to the target.

6. The method of claim 1, wherein the adhesive is adapted to be indirectly activated by the radiation.

7. The method of claim 1, wherein the adhesive comprises poly-anhydrides-co-imide.

8. The method of claim 1, wherein the plurality of particles comprise gold, gadolinium, glass, plastic, or combinations thereof.

9. The method of claim 1, wherein the target is located in a live subject, the method further comprising, while emitting the radiation toward the target, compensating for movement of the target caused by movement of at least a portion of the live subject.

10. The method of claim 1, further comprising obtaining an image of the visual fiducial mark and displaying the image on a display device.

11. The method of claim 10, further comprising using the displayed image to guide a practitioner to the target.

12. The method of claim 1, wherein intravenously providing plurality of particles comprises providing the plurality of particles into a blood vessel to transport in a blood stream at least some of the plurality of particles proximate to the target.

13. The method of claim 1, wherein emitting the radiation toward the target comprises emitting the radiation toward the target using one or more radiation beams shaped in a pattern corresponding to the predetermined pattern.

14. The method of claim 1, wherein emitting the radiation toward the target comprises activating a radiation source periodically.

15. The method of claim 1, wherein emitting the radiation toward the target comprises emitting an infrared radiation through the skin of a live subject.

16. The method of claim 9, wherein compensating for movement of the target comprises monitoring the target to detect the movement of the target and selectively activating a radiation source to emit the radiation towards the target when the target is stationary.

17. The method of claim 1, further comprising removing at least a portion of non-adhered particles from the blood stream.

18. The method of claim 1, further comprising emitting the radiation toward the target via a reflective device.

19. The method of claim 18, wherein the reflective device is a micro-mirror array.

20. The method of claim 18, wherein the reflective device is a transmissive LCD imager.

21. The method of claim 1, further comprising imaging the visual fiducial mark with an imaging system.

22. The method of claim 21, wherein the imaging system is an X-ray or a magnetic resonance imaging system.

* * * * *

UNITED STATES PATENT AND TRADEMARK OFFICE
CERTIFICATE OF CORRECTION

| | |
|---|---|
| PATENT NO. | : 9,682,156 B2 |
| APPLICATION NO. | : 12/580940 |
| DATED | : June 20, 2017 |
| INVENTOR(S) | : Kruglick |

It is certified that error appears in the above-identified patent and that said Letters Patent is hereby corrected as shown below:

On the Title Page

In item (74), under "Attorney, Agent, or Firm", in Column 2, Line 1,
delete "Xinova, LLC" and insert -- Xinova, LLC/Dorsey & Whitney LLP --, therefor.

In the Claims

In Column 13, Line 46, in Claim 1, delete "target b emitting" and
insert -- target by emitting --, therefor.

In Column 14, Lines 26-27, in Claim 12, delete "providing plurality" and
insert -- providing the plurality --, therefor.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*